United States Patent
Irani et al.

(10) Patent No.: US 9,085,965 B2
(45) Date of Patent: Jul. 21, 2015

(54) APPARATUS AND METHOD FOR IMPROVED FLUID SAMPLING

(75) Inventors: Cyrus Aspi Irani, Houston, TX (US); Mark A. Proett, Missouri City, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/188,616

(22) Filed: Jul. 22, 2011

(65) Prior Publication Data
US 2013/0020077 A1 Jan. 24, 2013

(51) Int. Cl.
*E21B 49/08* (2006.01)
*E21B 49/10* (2006.01)
*G01N 1/20* (2006.01)

(52) U.S. Cl.
CPC ............... *E21B 49/10* (2013.01); *E21B 49/081* (2013.01); *G01N 2001/2057* (2013.01)

(58) Field of Classification Search
CPC ....... E21B 49/081; E21B 49/10; E21B 27/00; G01N 1/2035; G01N 1/2042; G01N 2001/2057
USPC ............... 166/264, 169, 165, 162; 73/863.71, 73/864.62
See application file for complete search history.

(56) References Cited

U.S. PATENT DOCUMENTS

| | | |
|---|---|---|
| 5,644,076 A | 7/1997 | Proett et al. |
| 6,192,984 B1 * | 2/2001 | Schultz ..................... 166/264 |
| 7,059,179 B2 | 6/2006 | Proett et al. |
| 7,128,144 B2 | 10/2006 | Fox et al. |
| 7,197,923 B1 | 4/2007 | Wright et al. |
| 7,258,167 B2 * | 8/2007 | Shammai et al. ............. 166/264 |
| 7,472,589 B2 * | 1/2009 | Irani et al. .................. 73/152.23 |
| 7,568,521 B2 * | 8/2009 | Brown et al. ................... 166/66 |
| 7,581,435 B2 | 9/2009 | Pelletier |
| 7,650,937 B2 | 1/2010 | Fox et al. |
| 7,950,277 B2 * | 5/2011 | Irani et al. .................. 73/152.23 |
| 7,966,876 B2 * | 6/2011 | Irani et al. .................. 73/152.23 |
| 2007/0101808 A1 | 5/2007 | Irani et al. |
| 2007/0193377 A1 | 8/2007 | Irani et al. |
| 2008/0087470 A1 * | 4/2008 | Villareal et al. ................ 175/50 |
| 2008/0148838 A1 | 6/2008 | Irani et al. |

\* cited by examiner

*Primary Examiner* — Nicole Coy
(74) *Attorney, Agent, or Firm* — Alan Bryson; Baker Botts L.L.P.

(57) ABSTRACT

A sampling tool to sample formation fluids in a wellbore is disclosed. The sampling tool may include a sample chamber having a fluid inlet port and a tubular portion. A first piston may be sealably and movably disposed within the tubular portion. One or more surfaces of the first piston and the sample chamber may, at least in part, define a sample space. A second piston may be sealably and movably disposed within the first piston.

20 Claims, 3 Drawing Sheets

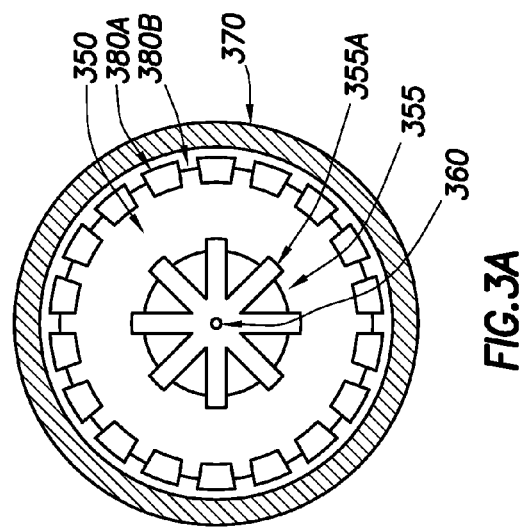
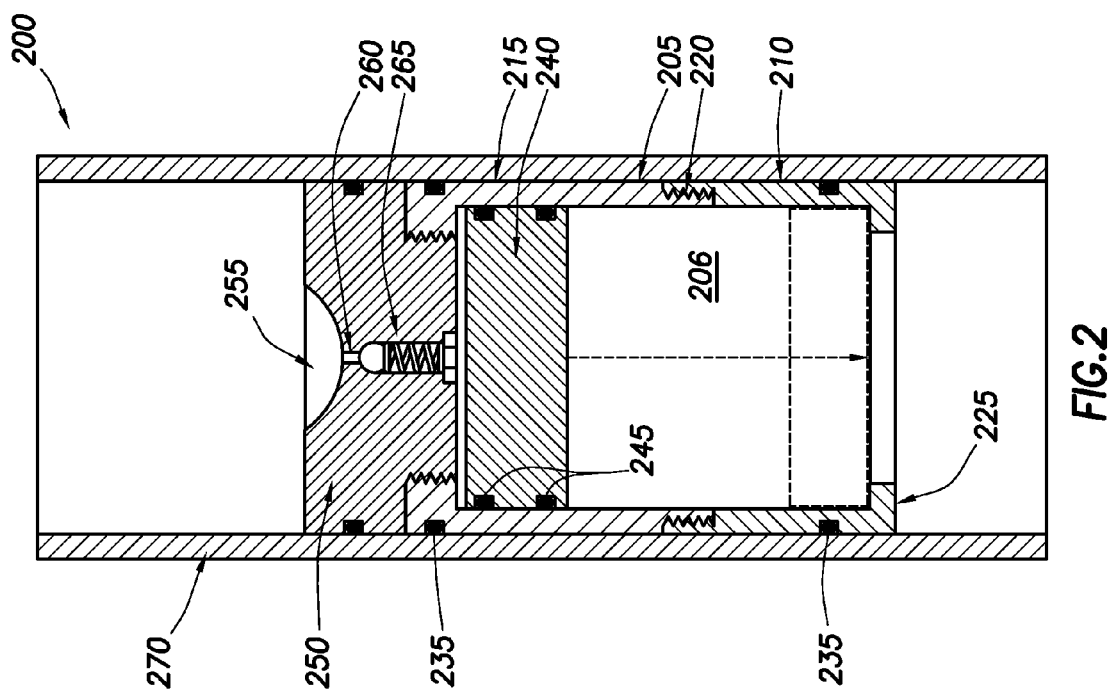

APPARATUS AND METHOD FOR IMPROVED FLUID SAMPLING

BACKGROUND

The present invention relates to testing and evaluation of subterranean formation fluids and, more particularly, to apparatus and method for improved fluid sampling.

It is well known in the subterranean well drilling and completion art to perform tests on formations penetrated by a wellbore. Such tests are typically performed in order to determine geological or other physical properties of the formation and fluids contained therein. For example, parameters such as permeability, porosity, fluid resistivity, temperature, pressure and saturation pressure may be determined. These and other characteristics of the formation and fluid contained therein may be determined by performing tests on the formation before the well is completed.

To evaluate prospects of an underground hydrocarbon reserve, a representative sample of the reservoir fluid may be captured for detailed analysis. In a typical sampling procedure, a sample of the formation fluids may be obtained by lowering a sampling tool having a sampling chamber into the wellbore on a conveyance such as a wireline, slick line, coiled tubing, jointed tubing or the like. When the sampling tool reaches the desired depth, one or more ports are opened to allow collection of the formation fluids. The ports may be actuated in a variety of ways such as by electrical, hydraulic or mechanical methods. Once the ports are opened, formation fluids travel through the ports and a sample of the formation fluids is collected within the sampling chamber of the sampling tool. After the sample has been collected, the sampling tool may be withdrawn from the wellbore so that the formation fluid sample may be analyzed.

It is important to obtain a sample of the formation fluid that is representative of the fluids as they exist in the formation with minimal contamination and without flashing the sample. Conditions that cause the fluid sample to approach or drop below saturation pressure create the possibility of asphaltene deposition and flashing of entrained gasses present in the fluid sample. There is need for some mechanism which will allow a zero flash sample to be taken but avoid the contamination of the sample.

FIGURES

Some specific exemplary embodiments of the disclosure may be understood by referring, in part, to the following description and the accompanying drawings.

FIG. 2 is a schematic cross-sectional view of a piston sampling system in accordance with an exemplary embodiment of the present disclosure.

FIG. 3A is a sectional view corresponding to Section 3A-3A in FIG. 3.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates to testing and evaluation of subterranean formation fluids and, more particularly, to apparatus and method for improved fluid sampling.

Illustrative embodiments of the present invention are described in detail herein. In the interest of clarity, not all features of an actual implementation may be described in this specification. It will of course be appreciated that in the development of any such actual embodiment, numerous implementation-specific decisions must be made to achieve the specific implementation goals, which will vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present invention, the following examples of certain embodiments are given. In no way should the following examples be read to limit, or define, the scope of the invention. Embodiments of the present disclosure may be applicable to horizontal, vertical, deviated, or otherwise nonlinear wellbores in any type of subterranean formation. Embodiments may be applicable to injection wells as well as production wells, including hydrocarbon wells. Embodiments may be implemented in which the tool is made suitable for testing, retrieval and sampling along sections of the formation. Embodiments may be implemented with various samplers that, for example, may be conveyed through flow passage in tubular string or using a wireline, slickline, coiled tubing, downhole robot or the like. The system of present disclosure may be suited for use with a modular downhole formation testing tool, such as the Reservoir Description Tool (RDT) by Halliburton, for example. Devices and methods in accordance with certain embodiments may be used in one or more of wireline, measurement-while-drilling (MWD) and logging-while-drilling (LWD) operations.

Figure 1:
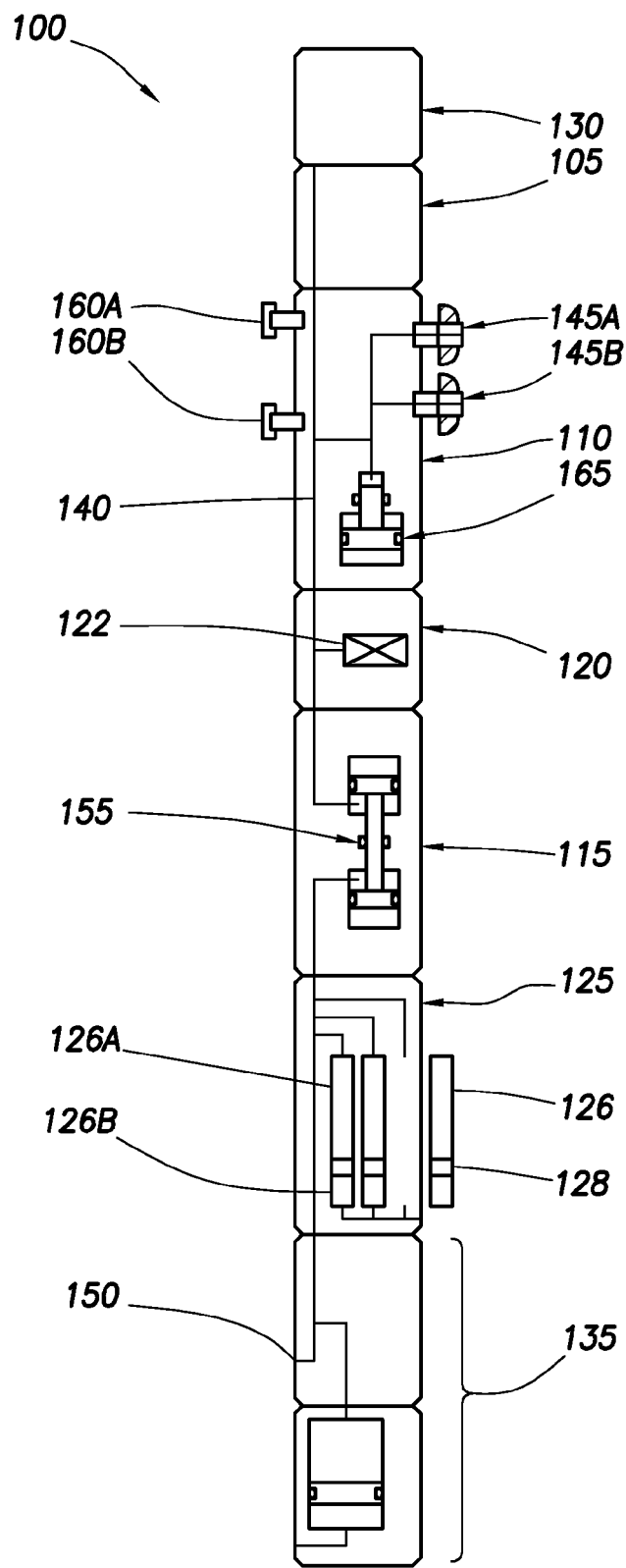
FIG. 1 is a cross-sectional schematic of a testing tool in accordance with an exemplary embodiment of the present disclosure.

FIG. 1 illustrates a cross-sectional schematic of a testing tool 100 in accordance with an exemplary embodiment of the present disclosure. The formation-testing tool 100 may be suitable for testing, retrieval and sampling along sections of a formation. The testing tool 100 may include several modules (sections) capable of performing various functions. For example, as shown in FIG. 1, the testing tool 100 may include a hydraulic power module 105 that converts electrical into hydraulic power; a probe module 110 to take samples of the formation fluids; a flow control module 115 for regulating the flow of various fluids in and out of the tool 100; a fluid test module 120 for performing different tests on a fluid sample; a multi-chamber sample collection module 125 that may contain various size chambers for storage of the collected fluid samples; a telemetry module 130 that provides electrical and data communication between the modules and an uphole control unit (not shown), and possibly other sections designated in FIG. 1 collectively as 135. The arrangement of the various modules, and additional modules, may depend on the specific application and is not considered herein.

More specifically, the telemetry module 130 may contain power conditioning electronics that supplies regulated power for the remaining sections of the testing tool 100. Each section may have its own process-control system and may function independently. The telemetry module 130 may provide a common intra-tool power bus, and the entire tool string may share a common communication bus that is compatible with other logging tools (possible extensions beyond testing tool 100 not shown). This arrangement may enable the tool to be combined with other logging systems.

The formation-testing tool 100 may be conveyed in a borehole by wireline (not shown), which may contain conductors for carrying power to the various components of the tool and conductors or cables (coaxial or fiber optic cables) for providing two-way data communication between tool 100 and an uphole control unit (not shown). The control unit preferably includes a computer and associated memory for storing programs and data. The control unit may generally control the operation of tool 100 and process data received from it during operations. The control unit may have a variety of associated peripherals, such as a recorder for recording data, a display for displaying desired information, printers and others. The use of the control unit, display and recorder are known in the art of well logging and are, thus, not discussed further. In an exemplary embodiment, telemetry module 130 may provide both electrical and data communication between the modules and the uphole control unit. In particular, telemetry module 130 may provide a high-speed data bus from the control unit to the modules to download sensor readings and upload control instructions initiating or ending various test cycles and adjusting different parameters, such as the rates at which various pumps are operating.

The flow control module 115 of the tool may include a pump 155, which may be a double acting piston pump, for example. The pump 155 may control the formation fluid flow from the formation into flow line 140 via one or more probes 145A and 145B. The number of probes may vary depending on implementation. Fluid entering the probes 145A and 145B may flow through the flow line 140 and may be discharged into the wellbore via outlet 150. A fluid control device, such as a control valve, may be connected to flow line 140 for controlling the fluid flow from the flow line 140 into the borehole. Flow line fluids may be pumped either up or down with all of the flow line fluid directed into or though pump 155.

The fluid testing section 120 of the tool may contain a fluid testing device, which analyzes the fluid flowing through flow line 140. For the purpose of this disclosure, any suitable device or devices may be utilized to analyze the fluid. For example, Halliburton Memory Recorder quartz gauge carrier may be used. In this quartz gauge the pressure resonator, temperature compensation and reference crystal are packaged as a single unit with each adjacent crystal in direct contact. The assembly is contained in an oil bath that is hydraulically coupled with the pressure being measured. The quartz gauge enables measurement of such parameters as the drawdown pressure of fluid being withdrawn and fluid temperature. Moreover, if two fluid testing devices 122 are run in tandem, the pressure difference between them may be used to determine fluid viscosity during pumping or density when flow is stopped.

The sample collection module 125 of the tool may contain one or more chambers 126 of various sizes for storage of the collected fluid sample. A collection chamber 126 may have a piston system 128 that divides chamber 126 into a top chamber 126A and a bottom chamber 126B. A conduit may be coupled to the bottom chamber 126B to provide fluid communication between the bottom chamber 126B and the outside environment such as the wellbore. A fluid flow control device, such as an electrically controlled valve, can be placed in the conduit to selectively open it to allow fluid communication between the bottom chamber 126B and the wellbore. Similarly, chamber section 126 may also contain a fluid flow control device, such as an electrically operated control valve, which is selectively opened and closed to direct the formation fluid from the flow line 140 into the upper chamber 126A.

The probe module 110 may generally allow retrieval and sampling of formation fluids in sections of a formation along the longitudinal axis of the borehole. The probe module 110, and more particularly the sealing pad, may include electrical and mechanical components that facilitate testing, sampling and retrieval of fluids from the formation. As known in the art, the sealing pad is the part of the tool or instrument in contact with the formation or formation specimen. A probe may be provided with at least one sealing pad providing sealing contact with a surface of the borehole at a desired location. Through one or more fluid flow channels or recesses in the sealing pad, fluids from the sealed-off part of the formation surface may be collected within the tester through the fluid path of the probe.

In the illustrated embodiment, one or more setting rams (shown as 160A and 160B) may be located generally opposite probes 145A and 145B of the tool. Rams 160A and 160B may be laterally movable by actuators placed inside the probe module 110 to extend away from the tool. Pretest pump 165 may be used to perform pressure tests by withdrawing small volumes of formation fluid and observing the pressure transients generated. Probes 145A and 145B may have high-resolution temperature compensated strain gauge pressure transducers (not shown) that can be isolated with shut-in valves to monitor the probe pressure independently. Pretest piston pump 165 may have a high-resolution, strain-gauge pressure transducer that can be isolated from the intra-tool flow line 140 and probes 145A and 145B. Finally, the module may include a resistance, optical or other type of cell (not shown) located near probes 145A and 145B to monitor fluid properties immediately after the fluids enter either probe.

With reference to the above discussion, the formation-testing tool 100 may be operated, for example, in a wireline application, where tool 100 is conveyed into the borehole by means of wireline to a desired location ("depth"). The hydraulic system of the tool may be deployed to extend one or more rams 160A and 160B and sealing pad(s) including one or more probes 145A and 145B, thereby creating a hydraulic seal between sealing pad and the wellbore wall at the zone of interest. To collect the fluid samples in the condition in which such fluid is present in the formation, the area near the sealing pad(s) may be flushed or pumped. The pumping rate of the piston pump 155 may be regulated such that the pressure in flow line 140 near the sealing pad(s) is maintained above a particular pressure to maintain a single phase fluid sample. Thus, while piston pump 155 is running, the fluid-testing device 122 may measure fluid properties. Device 122 may provide information about the contents of the fluid and the presence of any gas bubbles in the fluid to the surface control unit. By monitoring the presence of gas bubbles in the fluid, the pressure in the flow line 140 may be constantly adjusted so as to maintain a single-phase fluid in the flow line 140. These fluid properties and other parameters, such as the pressure and temperature, may be used to monitor the fluid flow while the formation fluid is being pumped for sample collection. When it is determined that the formation fluid flowing through the flow line 140 is representative of the in situ conditions, the fluid may then be collected in the fluid chamber(s) 126.

When tool 100 is conveyed into the borehole, the borehole fluid may enter the lower section of fluid chamber 126B. This may cause piston 128 to move inward, filling bottom chamber 126B with the borehole fluid. This may be due to the hydrostatic pressure in the conduit connecting bottom chamber 126B and a borehole being greater than the pressure in the flow line 140. Alternatively, the conduit may be closed by an electrically controlled valve, and bottom chamber 126B may be allowed to be filled with the borehole fluid after tool 100 has been positioned in the borehole. To collect the formation fluid in chamber 126, the valve connecting bottom chamber 126B and flow line 140 may be opened and piston pump 155 may be operated to pump the formation fluid into flow line 140 through the inlets of the sealing pad(s). As piston pump 155 continues to operate, the flow line pressure may continue to rise. When the flow line pressure exceeds the hydrostatic pressure (pressure in bottom chamber 126B), the formation fluid may start to fill in top chamber 126A. When the upper chamber 126A has been filled to a desired level, the valves connecting the chamber with both flow line 140 and the borehole may be closed, which may ensure that the pressure in chamber 126 remains at the pressure at which the fluid was collected therein.

In certain alternative embodiments, the pump 155 and/or another pump may be positioned "downstream" of the sample chamber 126 such that it is fluidically coupled to the sample chamber 126 via the bottom chamber 126B. In such embodiments, the downstream pump may provide the necessary pressure and fluid movement to draw fluid into the sample chamber 126. The downstream pump may be used alone or in combination with an upstream pump that may be configured as pump 155.

FIG. 2 illustrates a schematic cross-sectional view of a piston sampling system 200 in accordance with an exemplary embodiment of the present disclosure. The piston sampling system 200 may be employed in a variety of sampling tool configurations. For example without limitation, the piston sampling system 200 may be implemented in the tool 100, depicted in FIG. 1, in place of or in combination with piston system 128. However, it should be clearly understood that the principles of this disclosure are not limited to use with a particular tool or methods. Instead, the principles of this disclosure are applicable to wide variety of tools and methods.

With traditional samplers, there is a dead volume (e.g., up to 20 cc) between the sampler and the pump that will charge the sampler when fluid is fit to be sampled. The dead volume can be extremely detrimental to collecting a zero shock sample, as the first few cc of sample transiting between the pump and the sampler may flash in this space. This flashing could result in asphaltenes being released from solution, undermining the quality of the rest of the sample being collected. To avoid this flashing from taking place, it is customary to fill this dead space with some neutral and preferably incompressible fluid such as water. Unfortunately, the filler fluid then becomes part of the collected sample and can be viewed as a contaminant. However, certain embodiments of the present disclosure allow for a zero flash, or substantially zero flash, sample to be taken while avoiding or substantially minimizing the contamination of the sample.

The piston sampling system 200 may include a primary piston 205 surrounding a cavity 206. The primary piston 205 may include one or more sections. In the example depicted, the primary piston 205 includes sections 210 and 215 that may be coupled together, for example, via a threaded connection portion 220. At one end, the primary piston 205 may form a retaining lip 225. At the opposing end, the primary piston 205 may include a threaded connection portion 230.

The primary piston 205 may be configured to seat one or more exterior seals 235 for sealing against a tubular 270 exterior to the primary piston 205. By way of non-limiting example, the tubular 270 may correspond to the fluid chamber(s) 126 in the example of FIG. 1. The seals 235 may be o-ring seals, for example. In the example of FIG. 2, two exterior seals 235 are disposed proximate to opposing ends of the primary piston 205. The exterior seals 235 may hold the primary piston 205 in place within the exterior tubular and seal one end of the primary piston 205 from other end.

A secondary piston 240 may be disposed inside the primary piston 205. The secondary piston 240 may be configured to seat one or more seals 245 for sealing against an inner face of the primary piston 205. Like the seals 235, the seals 245 may be o-ring seals, for example, and may be seated at opposing ends of the secondary piston 240. The primary piston 205 and secondary piston 240 may be configured to allow the secondary piston 240 to slide along a length of the primary piston 205 depending on fluid pressure. Movement of the secondary piston 240 may be limited at one end by the retaining lip 225, which may be formed to have an inner dimension less than an outer diameter of the secondary piston 240.

The primary piston 205 may include a cap 250 that may be connected via the threaded connection portion 230. The cap 250 may include a hollow portion 255 for a mixing ball (not shown). The mixing ball may be a ball of appropriate diameter to be half-contained when seated within the cavity 255 of the cap 250. When sampler chamber 126 is mounted in a rocking stand and oscillated, the mixing ball can be expected to roll back and forth in the upper chamber 126A. This rolling action may serve to provide mixing of the contents of upper chamber 126A, thus homogenizing the collected sample and facilitating the transfer of a representative sample. The mixing ball may be of some material softer than the material that comprises the chamber 126 so that the rolling action of the ball not scratch the surface of the chamber 126. Consequently, the mixing ball can be made of some soft material such as brass or the like, or even be of steel provided it is coated with a softer polymeric material such as Teflon so as to protect the chamber 126 during mixing.

The cap 250 may include a narrow-diameter passage 260 and a one-way valve 265 for moving fluid from the hollow portion 255 into the space above the secondary piston 240. The one-way valve 265, for example without limitation, may comprise a spring-loaded ball-shaped element, as depicted, or a spring-loaded dart-shaped element. The ball-shaped or drat-shaped element may be made of some soft material, such as Teflon or PEEK, that sits snugly in a suitably tapered metal receptacle. In the case of a dart-shaped element, the element may be positioned in the receptacle with the point of the dart facing up towards the top of the cap 250. In this configuration, the ball or dart will act like a one-way check valve, allowing movement of fluid through the passage 260 in the direction from 255 towards the space present above the secondary piston 240. However, the fluid contained between the secondary piston 240 and the cap 250 may be restricted from exiting past the ball or dart of valve 265 because the ball or dart may seat against its tapered metal seat and provide an obstruction for the fluid to flow. This may cause any spurious fluid trapped in the cavity above the secondary piston 240 to stay trapped and, consequently, isolated from the main sample collected outside and above the primary piston 205. In this trapped configuration, only some external intervention that causes the check ball or check dart of valve 265 to come off its seat will allow the fluid trapped inside the cavity above the secondary piston 240 to be released.

In order to eliminate sample contamination during transfer, a sample may be collected over the piston sampling system 200 contained in a tubular section 270 that collects the sample. For example, in the non-limiting exemplary embodiment of FIG. 1, the tubular section that collects the sample may be one or more fluid chambers 126, and the piston sampling system 200 depicted in FIG. 2 may be implemented in place of or in combination with the piston 128. The piston sampling system 200 may isolate the sample from fluids injected below the piston sampling system 200 to move the sample out during sample transfer. For example, consider a reservoir fluid with a downhole pressure of 10,000 psi that is to be captured. When the sampling tool is ready to collect a sample, the internal configuration of the tool may be as follows. The primary piston 205 may be at the top of its stroke at the top of the tubular section where the sample is to be collected (e.g., chamber 126). The secondary piston 240 also may be at the top of its stroke, as depicted in FIG. 2. Both pistons may have fluid, such as borehole fluid or gas (e.g., nitrogen gas), at high pressure behind them, keeping them at the top of their stroke. In some embodiments, where nitrogen gas is to be used for pressure maintenance after sampling and during recovery to the surface, the gas may be isolated between primary piston 205 and secondary piston 128, with gas pressure serving to keep the secondary (isolation) piston 240 at the top of its stroke. The gas may be compressed to the high pressure by the movement of a piston 128 that may be exposed to surrounding fluids such that any pressure present in the surrounding fluids will act on the piston 128 and serve to compress the trapped gas to the same pressure as the surrounding fluids.

In order to collect a sample, a hydraulic pump (e.g., pump 155) may be used to physically pressurize the sample to a pressure significantly above the fluid pressure below the secondary piston 240 in cavity 206, and thus move the sample into the sample chamber. However, the space between the pump and the sample chamber has a dead volume channel, which may be between 15 and 20 cc, for example. In order to prevent the shock of volume expansion when the transferred fluid first accesses this channel, it is customarily filled with some inert fluid such as water or gas that presents opportunities for contamination and needs to be removed from contact with the collected sample. Once the sample pressure exceeds the gas pressure on the opposing side of the primary piston 205, the sample will begin to flow into the sample chamber. Depending on the volume of the space created between the secondary piston 240 and the primary piston 205, the initial volume (e.g., the first 15 cc) of inert fluid injected into the sample chamber may act on the secondary piston 240 and move it to the end of its stroke (indicated by the dashed arrow in FIG. 2). The initial volume of inert fluid may move into the space created inside the primary piston 205 by the movement of the secondary piston 240 and may be isolated from the rest of the sample entering the sample chamber. Once the secondary piston 240 has reached the end of its stroke, any additional sample pumped into the sample chamber may serve to move the primary piston 205 down with respect to the sample chamber until the desired sample is collected. During the sample collection process, the primary piston 205 and secondary piston 240 may move in tandem.

During sample transfer, the position of the primary piston 205 may be monitored. For example, the secondary piston 240 may include one or more magnets, which, in conjunction with conventional monitoring equipment, would enable the position of the primary piston 205 to be monitored. For example, the piston 240 can have imbedded in it a powerful rare earth magnet such that its magnetic field will readily penetrate the stainless steel material of the sampler 126. Consequently, a Gauss meter capable of detecting the presence of a magnetic field and its intensity can be positioned outside the case of the sampler 126 and used to pinpoint the location of the magnet and subsequently the location of the pistons 240 and 205. When primary piston 205 has bottomed out, the transfer process may be stopped. Until the primary piston 205 bottoms out, irrespective of the transfer pressure, the secondary piston 240 will not move relative to the primary piston 205 because the pressure differential may be the same across both pistons. Certain embodiments may further include a locking mechanism such that, at the bottom of its stroke, the secondary piston 240 may be mechanically locked in place, thereby eliminating the possibility of its movement during sample transfer.

In the exemplary embodiment depicted in FIG. 2 is an alternative of including a one-way valve 265 in the cap 250 of the primary piston 205. As depicted, the cap 250 may have a hollow 255 for accommodating a mixing ball, and also a narrow diameter passage 260 for moving fluid from the sample space (i.e., the space above the cap 250) into the trapping space (i.e., the space between the cap 250 and the secondary piston 240). This valve 265 may be configured so that fluid could only move from the sample space to the trapping space, but not in the reverse direction. Consequently, once the contaminant has entered the trapping space, it will no longer be able to access the sample space and act as a contaminant. A small setscrew or other pressure relief mechanism (not shown) may be included in the body of the primary piston 205 to relieve the pressure trapped inside the primary piston 205 after the sample transfer step has been concluded.

Figure 3:
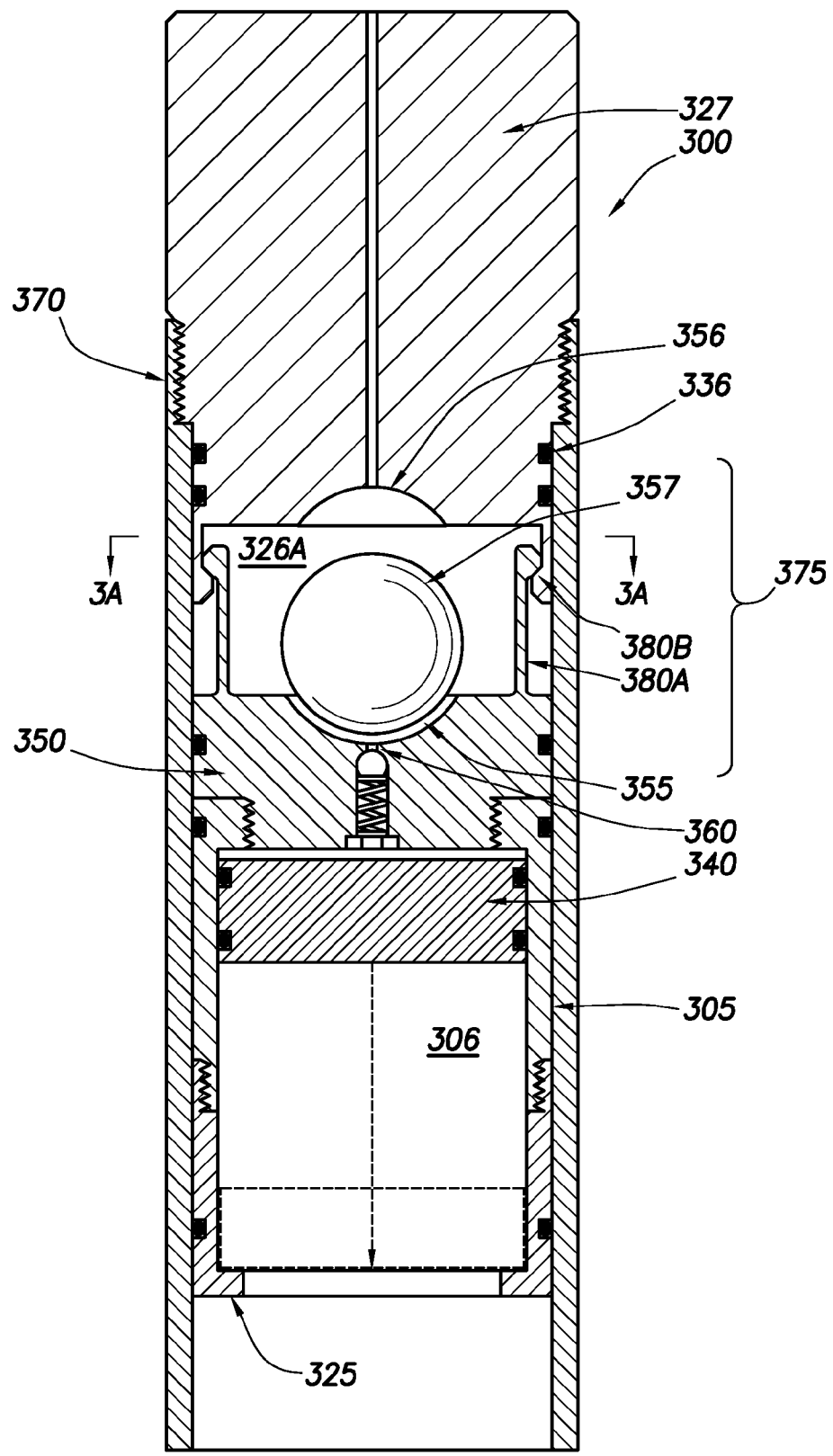
FIG. 3 is a schematic cross-sectional view of a piston sampling system in accordance with an exemplary embodiment of the present disclosure.

FIG. 3 illustrates a schematic cross-sectional view of a piston sampling system 300, in accordance with an exemplary embodiment of the present disclosure. FIG. 3A is a sectional view corresponding to Section 3A-3A in FIG. 3. The piston sampling system 300 builds on the piston sampling system 200, and like reference numbers indicate like parts. The piston sampling system 300 comprises an exemplary retainment assembly 375 to retain and to release the primary piston 305, including the cap 350 and other associated movable parts, during the sampling process. In particular, the retainment assembly 375 may ensure that the cavity 306 of the primary piston 305 may be completely filled before the primary piston 305 moves downward. And, while the retainment assembly 375 illustrates one particular example, it should be understood that other retainment assemblies could be employed in accordance with the present disclosure to ensure that the cavity 306 of the primary piston 305 may be completely filled before the primary piston 305 moves downward.

The retainment assembly 375 may include one or more retainment members 380A coupled to the cap 350 of the primary piston 305. The retainment members 380A may be removably attached to, fixedly attached to, or formed integrally with the cap 350 in any suitable manner. The retainment members 380A may be flexible rods or other extensions designed to flex inward in an elastic manner. In the retaining state, the retainment members 380A may extend from the cap 350 and seat within a groove 380B of a chamber cap 327. The surfaces of the retainment members 380A and groove 380B may be chamfered as depicted or otherwise formed to let the tabs of the retainment members 380A slide on the lip of the groove 380B to facilitate transitioning between the retaining and non-retaining states, as described below.

The chamber cap 327 may be threadedly coupled to the top portion of the tubular 370 and may have a fluid passage extending therethrough to allow passage of fluid from an exterior space to the sampling space 326A. The chamber cap 327 may be configured to seat one or more exterior seals 336 for sealing against the tubular 370. The chamber cap 327 may include a hollow portion 356 corresponding to a hollow portion 355 of the cap 350, each shaped to receive a mixing ball 357 disposed therebetween. The hollow portion 355 may include one or more flow channels 355A to prevent the ball 357 from seating on the small opening of passage 360. In various embodiments, the small opening may be offset from the hollow portion 355 or other stand-off means may be employed.

When in the retaining state, the retainment members 380A interface with the groove 380B to require additional friction for the primary piston 305 to move downward. As the space between the secondary piston 340 and the cap 350 is filling and consequently contacts the bottom retaining lip 325, the hydraulic force increases so that the retainment members 380A flex inward until they slip past the smaller diameter lip of the groove 380B. This allows the secondary piston 340 to fully displace and the space between the secondary piston 340 and the cap 350 to fill with contaminated fluid, before the primary piston 305 moves and the chamber 326A is filled.

To return the primary piston 305 and the retainment assembly to the retaining state, hydraulic pressure may be applied to the lower end as previously described with respect other embodiments. But, when the retainment members 380A reach the smaller diameter lip of the groove 380B, additional pressure may be applied to cause the retainment members 380A to flex inwardly until they lock in place past the smaller diameter lip of the groove 380B.

Accordingly, certain embodiments of the present disclosure allow for a zero flash, or substantially zero flash, sample to be taken while avoiding or substantially minimizing the contamination of the sample. And even though the figures depict embodiments of the present disclosure in a vertical orientation, it should be understood by those skilled in the art that embodiments of the present disclosure are well suited for use in a variety of orientations. Accordingly, it should be understood by those skilled in the art that the use of directional terms such as above, below, upper, lower, upward, downward and the like are used in relation to the illustrative embodiments as they are depicted in the figures, the upward direction being toward the top of the corresponding figure and the downward direction being toward the bottom of the corresponding figure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee. The indefinite articles "a" or "an," as used in the claims, are defined herein to mean one or more than one of the element that it introduces.

What is claimed is:

1. A sampling tool to sample formation fluids in a wellbore, the sampling tool comprising:
   a sample chamber having a fluid inlet port and a tubular portion;
   a first piston sealably and movably disposed within the tubular portion, wherein
   one or more first surfaces of the first piston and the sample chamber, at least in part, define a sample space; and
   at least one of the one or more first surfaces of the first piston comprises a cap disposed between the sampling space and the trapping space;
   a cavity within the first piston; and
   a second piston sealably and movably disposed within the cavity, the second piston at least partially defining a trapping space within the cavity.

2. The sampling tool of claim 1, wherein the first and second pistons receive a first fluid volume via the fluid inlet port to separate the first fluid volume from a second fluid volume without flashing the second fluid volume.

3. The sampling tool of claim 2, further comprising the trapping space defined, at least in part, by the first and second pistons, to receive the first fluid volume.

4. The sampling tool of claim 3, comprising a valve to allow movement of the first fluid volume from the sample space to the trapping space and to, at least in part, retain the first fluid volume in the trapping space after the first fluid volume enters the trapping space.

5. The sampling tool of claim 3, wherein the cap comprises a removably connected cap.

6. The sampling tool of claim 5, wherein the cap comprises:
   a passage to enable movement of the first fluid volume from the sample space to the trapping space; and
   a hollow to receive a mixing ball disposed with the sample chamber.

7. The sampling tool of claim 1, wherein the sample chamber comprises a wellbore fluid inlet that enables entry of wellbore fluid into a space generally opposite the sampling space.

8. The sampling tool of claim 1, further comprising:
   a retaining surface of the first piston that limits a stroke of the second piston;
   a retainment assembly to retain the first piston at least until the second piston contacts the retaining surface, wherein the retainment assembly comprises a flexible retainment member extending from the first piston to interface with a stationary chamber cap.

9. A piston system to sample formation fluids in a wellbore, the piston system comprising:
   a tubular having an inlet to be in fluid communication with a first fluid and second fluid;
   a first piston within the tubular to receive the first fluid;
   a cavity within the first piston;
   a second piston to move within the cavity and create a first space for the first fluid in the cavity to separate the first fluid from the second fluid; and
   wherein the first piston comprises a cap disposed between the first space and a second space within the tubular for the second fluid.

10. The piston system of claim 9, wherein the first fluid is separated from the second fluid without flashing the second fluid.

11. The piston system of claim 9, comprising a valve to allow movement of the first fluid to the first space and to, at least in part, retain the first fluid in the first space after the first fluid enters the first space.

12. The piston system of claim 9, wherein the cap comprises a removably connected cap, wherein the cap comprises a passage to enable movement of the first volume from the second space to the first space.

13. The piston system of claim 12, wherein the cap comprises a hollow to receive a mixing ball disposed with the tubular.

14. The piston system of claim 9, wherein the tubular comprises a wellbore fluid inlet that enables entry of wellbore fluid into a space generally opposite the second space.

15. The piston system of claim 9, further comprising:
a retaining surface of the first piston that limits a stroke of the second piston;
a retainment assembly to retain the first piston at least until the second piston contacts the retaining surface, wherein the retainment assembly comprises a flexible retainment member extending from the first piston to interface with a stationary chamber cap.

16. A method of sampling a formation fluid in a wellbore, the method comprising:
lowering a sampling tool into a borehole, the sampling tool comprising:
a sample chamber having a fluid inlet port and a tubular portion;
a first piston sealably and movably disposed within the tubular portion, wherein
one or more surfaces of the first piston and the sample chamber, at least in part, define a sample space; and
at least one of the one or more first surfaces of the first piston comprises a cap disposed between the sampling space and a trapping space; and
a cavity within the first piston; and
a second piston sealably and movably disposed within the cavity, the second piston at least partially defining the trapping space within the cavity;
initiating a sampling mode wherein a first fluid volume received into the sample space via the fluid inlet port is separated from a second fluid volume and contained in the trapping space, so that the second fluid volume is contained in the sample space.

17. The method of claim 16, wherein the first and second pistons cooperate to separate the first fluid volume from the second fluid volume without flashing the second fluid volume.

18. The method of claim 16, wherein the sampling tool comprises a fluid control device, and the method further comprises the step of regulating the drawdown of fluids in the sampling tool using the fluid control device.

19. The method of claim 16, wherein the cap comprises a removably connected cap.

20. The method of claim 19, wherein the cap comprises a passage to enable movement of the first fluid volume from the sample space to the trapping space.

* * * * *